United States Patent [19]

Lee

[11] Patent Number: 5,110,804

[45] Date of Patent: May 5, 1992

[54] NON-TOXIC INSECTICIDE COMPOSITION AND METHOD FOR KILLING SPECIFIC INSECTS

[75] Inventor: Merlin Lee, Orcutt, Calif.

[73] Assignee: Agrisystemen Limited, Hong Kong, Hong Kong

[21] Appl. No.: 420,120

[22] Filed: Oct. 10, 1989

[51] Int. Cl.$^5$ .................. A61K 31/715; A61K 35/78; A01N 25/00

[52] U.S. Cl. ................... 514/60; 424/195.1; 424/405; 424/406

[58] Field of Search ............. 424/195.1, 405, 406; 514/58, 60

[56] References Cited

U.S. PATENT DOCUMENTS

| | | | |
|---|---|---|---|
| 4,307,115 | 12/1981 | Klopping | 424/327 |
| 4,384,988 | 5/1983 | Schoenholz | 252/610 |
| 4,755,397 | 7/1988 | Eden | 427/213.3 |
| 4,812,445 | 3/1989 | Eden | 514/60 |
| 4,818,534 | 4/1989 | Levy | 424/404 |
| 4,911,952 | 3/1990 | Doane | 427/213.31 |

OTHER PUBLICATIONS

Farmline Magazine, vol. IX, No. 5, p. 15, np(1) May 1988.

*Primary Examiner*—Ronald W. Griffin
*Assistant Examiner*—Ralph Gitomer
*Attorney, Agent, or Firm*—Allegretti & Witcoff, Ltd.

[57] ABSTRACT

Non-toxic insecticide composition for killing white flies, scale insects and mealy bugs comprising a viscous aqueous solution of modified cold water swelling corn starch consisting essentially of amylopectin prepared from intact fully-swollen corn granules as determined by microscopic analysis. The solution is used to entrap and/or asphyxiate the insects.

12 Claims, No Drawings

NON-TOXIC INSECTICIDE COMPOSITION AND METHOD FOR KILLING SPECIFIC INSECTS

BACKGROUND OF THE INVENTION

This invention relates to non-toxic insecticides, especially effective for killing white flies, scale insects, and mealybugs, including their eggs, instars and pupae. All of these insects belong to the order homoptera. They all exude waxy secretions, sometimes referred to as honeydew, which covers their bodies and protects their eggs from chemical insecticides. There are various species within these generic groups, but all of them are characterized by the protective waxy secretions. White flies are minute insects rarely over 2 or 3 millimeters in length. The adults are winged and the wings are covered with this white dust or waxy material. White flies are most abundant in the tropics and sub-tropics. The most important white fly species in this country are those that attach citrus trees and greenhouse plants. The damage is done by sucking sap from the leaves. Severe damage to greenhouse crops also is inflicted by virus transmitted by white flies. This virus called beat pseudo yellows virus (BPYV) induces stunting, unthriftiness and interveinal yellowing of the plants. This viral disease transmitted by white flies is devastating to growers of lettuce particularly. It is estimated that white flies are vectors for 70 different viruses which stunts tomatoes, cause squash leaves to curl and drains beets of their sugar. White flies also cause major losses of cottom crops.

Scale insects look very much like small gnats. The females remain under the scale covering when they become adult and produce their eggs or give birth to their young there. These insects injure plants by sucking sap and when numerous, may kill the plant.

Mealybugs get their name from the mealy or waxy secretions that cover their bodies. There are a number of species within this group which attack citrus fruits and greenhouse plants. The females excrete large quantities of honeydew.

THE PRIOR ART

There are literally hundreds of toxic organic compounds available which are used to kill insects. These include organic derivatives of phosphorous, of carbamic acid, of nitrophenols and other miscellaneous compounds. These chemicals are mixed with anti-caking agents, corn starch, wetting agents, diluents and other ingredients to facilitate their preparation and use in application to the crops by farmers. U.S. Pat. No. 4,307,115 is a typical insecticide consisting of 90–94% methomyl as the active ingredient, in admixture with fillers such as corn starch, clay and surfactants. Such insecticides attack the central nervous system and kill by paralysis or they attack the metabolic cycle of the insect and disrupt the process causing death. These materials are not effective in penetrating the waxy film or covering of white flies, scale and mealybugs. Most are able to survive exposure to toxic insecticides. Chemical formulations especially designed to penetrate the protective waxy coating have severely damaged or killed plants to which they were applied.

In recent years, insects have built up an immunity to toxic insecticides which prompted farmers to use larger and larger quantities of these toxic materials. Government regulations set limits on the amounts of chemical residues left on fruits and vegetables to insure that they are well below the danger levels. Despite regulations, consumer groups are claiming that pesticides could result in tens of thousands of cancer cases over the next 50 years. According to the Environmental Protection Agency, use of pesticides, fungicides, herbicides, insecticides and plant growth regulators have more than doubled during the period 1969-1989 to about 820 million pounds annually. Fruits imported into the United States have been confiscated and gone to waste because of alleged contamination by chemical residues. These insecticides are very expensive and in some instances, constitute 25% of the farmers' expense in growing a crop. The use of toxic chemicals also puts at risk persons who apply them in the fields and increases liability insurance rates for farmers. Another disadvantage of toxic insecticides is that they kill beneficial insects.

THE INVENTION

It is the object of this invention to obviate the use of toxic chemicals and all of their attendant disadvantages. A further object is to provide a non-toxic insecticide which is completely effective in killing white flies, scale insects, mealybugs and their eggs, instars and pupae. The insecticide must not be phytotoxic or harmful to the environment. Furthermore, the insecticide must be simple to use and to apply using conventional spray equipment. It is also desirable to provide a non-toxic insecticide of this kind which is not expensive.

These objects are achieved by using a composition which kills the insects by physical rather than chemical means. The compositions of the invention are solutions which form sticky films over the insects to immobilize them and entrap the adults together with their eggs, pupae and instars. The film, furthermore, closes off the spiracles of the tracheal system through which the insect receives oxygen and discharges carbon dioxide. Consequently, these films will kill the insect not only by entrapping it so that it becomes immobile and dies, but also by asphyxiating it. The film is deposited on the leaves and stems of plants which carry the insects.

One of the remarkable features of the films of the invention is that they dissolve, coalesce or absorb the waxy secretion which is exuded by the insects. The insects, their eggs, larvae, pupae and instars become an integral part of the sticky film. As the film dries, it shrinks and falls from the leaf of the plant onto the ground. The film is biodegradable in addition to being harmless to humans or other animals. No toxic residue is left in the soil.

The films of the invention are prepared by dissolving starch in water to prepare a solution having a kinematic viscosity ranging from 3.4 to 800 centistokes, preferably from 70 to 800. The viscosity is critical. If the viscosity is less than about 3.4 centistokes, the film will not adhere to the insects and to the leaves and stems of the plants. If the viscosity is greater than about 800 centistokes, it will not coalesce with the waxy material and form the continuous film necessary to entrap the insects. Solutions of higher viscosities become more difficult to spray, produce a non-uniform spray pattern and uneven film thickness.

Pregelatinized cold water swelling corn starch is the preferred starch for use in preparing the solutions of the invention. This material is harmless and is designated "food starch, modified" as approved by the Food and Drug Administration as a food additive (21 CFR 172.892). The modified starch is prepared from intact fully swollen (rather than crushed) waxy corn granules as determined by microscopic analysis. It consists essentially of amylopectin, a highly branched polymer of α-D-glucopyranosyl units containing 1→4 links with 1→6 links at branch points, which may be modified by light cross linking. The average branch length is about 25 D-glucose units. Since this product contains no amylose it will not retrograde or gel under normal storage conditions. It has a high molecular weight between 50,000 and $10^6$.

This pregelatinized cold water swelling corn starch is especially suitable for use on the farm where hot water is not generally available. These solutions are prepared in 50 or 100 gallon tanks. It is impractical to heat water to 210° in order to dissolve unmodified starch. Unmodified starch is operable for purposes of the invention if it can be dissolved and effectively applied by spraying. The preferred pregelatinized cold water swelling corn starch useful for this invention is commercially available under the tradename Ultra-Tex 2 sold by National Starch & Chemical Corporation of Bridgewater, N.J. Solutions having the desired viscosity have a solids content of from 2 to 5.2% of Ultra-Tex 2.

Many other modified starches have been found to be inoperable for purposes of the invention, including a waxy maize cook up starch (National 465, National Firm-Tex) and National Purity Gum 59 and National Ultra Sperse. These starches are water soluble but do not form films.

The starch solutions of the invention may be modified by the addition of one part of borated dextrin for each four or five parts of starch by weight. The borated dextrin goes into solution with the starch and improves the quality of the film deposited on the leaves and stems of the plant. The film is of such viscosity and adhesiveness that it adheres even to the undersides of the leaves and penetrates into the leaf pattern producing a reproduction of the leaf design. This characteristic of the film results in entrapment of all foreign materials on the surface of the plant, including the insects, their eggs, instars and pupae. The foreign materials become an integral part of the film. As the water evaporates from the film, the film shrinks and subsequently drops to the ground carrying the foreign materials with it.

The starch solution is applied to the plants through a nozzle of conventional spraying equipment. It is preferred that the pressures not exceed 600 or 700 psi. If the viscosity of the solution exceeds about 800 centistokes, it becomes too thick to spray through a nozzle which produces droplets of the desired size for deposition on the leaves and stems of the plants. Furthermore, the very high viscosity solution does not flow down around the insects to entrap them securely. Solutions of modified cold water swelling corn starch should contain in the range of 2 to 5% solids which produces viscosities ranging from 3.5 centistokes to about 800 centistokes. Above 4% solids, the solutions increase very rapidly in viscosity. At 6% solids, the viscosity reaches about 10,000 centistokes which is much too viscous for purposes of this invention. A preferred solution of modified cold swelling corn starch contains about 4.2%. This solution may be modified by adding 1% borated dextrin to increase the total solids to 5.2%. This combination produces a solution having a viscosity of about 800 centistokes.

The water, in which all solutions of the invention are prepared, contains a surfactant wetting agent, e.g. alkyl-/aryl polyether alcohols, polyethylene oxide esters (or ethers) of fatty acids, alkyl/aryl sulfonates, alkyl sulfates and the like. The surfactant is preferably present in the amount of about 0.8%. These surface active agents are well known in the art for use in preparing dispersions of insecticides. In the solutions of the invention, the surfactants assist in causing the solution droplets to spread out on waxy leaves and penetrate the waxy protective coating on the insects and their eggs.

If obtaining hot water is no problem, unmodified corn starch can be used without additives to achieve the purposes of the invention. Solutions prepared in hot water containing from 2.5 to 3.75% solids are preferred. These solutions have a viscosity of 90 centistokes to 810 centistokes, respectively. These solutions are not as effective as the modified cold water starch in entrapping the insects and forming a film which cuts off the oxygen supply. There are available on the market spray guns used in the application of plastic foam, which heat the material being sprayed to above 200° F. A slurry of unmodified starch can be introduced into a stream of hot water for a controlled residence time and released as a film-forming solution.

The following specific examples illustrate the invention.

EXAMPLE 1

A solution was prepared by dissolving 20 grams of modified cold water swelling corn starch (Ultra-Tex 2) in 480 grams of water. This solution has a viscosity of 72.4 centistokes. The solution was put into a conventional agricultural sprayer and sprayed through a nozzle on geranium plants having white flies, eggs, instars and pupae on the leaves thereof. The sprayer has a hollow cone tip nozzle with a swivel connector to facilitate spraying the bottoms of the leaves and stems. At 60 psi the droplets are about 340 microns in size. As pressure increases, the droplets become smaller into the range of 50-100 microns. The desired droplet size should not exceed 400 microns which insure adequate plant coverage and desired film thickness. The sticky solution covered both the top and bottom of the leaves and adhered to the leaves in a film to entrap the white flies, eggs, instars and pupae. After about 4 hours, the film had dried, shrunk, and fell off the leaves to the ground. Examination of the plant through magnification indicated that no insects or their eggs, instars and pupae remained on the leaves. The film separated from the leaves contained all of the white flies, eggs, instars and pupae that had previously been on the leaves. Remarkably, there was no foreign matter at all on the leaves after the film dropped off. The solution coalesced with the waxy secretion of the insects and was effective in killing all of them. The examination was confirmed by photographs taken before and after spraying, which photos showed clearly at 30 times actual size the condition of the insects at both stages.

EXAMPLE 2

A solution of modified cold water swelling starch (Ultra-Tex 2) was prepared by adding 20 grams of that starch and 5 grams of borated dextrin to 480 grams of water. This solution, containing 5.2% solids, had a viscosity of about 800 centistokes. The solution was sprayed as described in Example 1 on a plant carrying mealybugs. The solution formed a film over and around the bugs. As in Example 1, the film dried and fell and/or was blown off the leaves of the plant. The film formed from this solution, after drying, was firmer than the film formed from the modified corn starch alone and carried an impression of the leaf design. Examination through magnification indicated that active mealybugs prior to spraying had all died even before the film had dried completely.

EXAMPLE 3

A solution was prepared by dissolving 10 grams of modified cold water swelling corn starch (Ultra-Tex 2) in 480 grams of water. This produced a relatively thin solution having a viscosity of 3.4 centipoises. This solution sprays more readily, but the deposited film is thinner and not as strong as the one which results from solutions containing higher solids. The solution was sprayed on a plant carrying white flies as in Example 1. After about 5 hours, the film had dried and examination under magnification indicated most of the flies and their eggs, instars and pupae were immobilized and died in the film.

EXAMPLE 4

A solution was prepared from modified cold water swelling corn starch (Ultra-Tex 2) by dissolving 25 grams of the starch in 480 grams of water. This produced a solution having a viscosity of 785 centistokes. The solution was sprayed as described in Example 1 on a plant which contained scale insects. The results achieved were as described in Example 1. This composition adheres well to the leaves and shrinks upon drying to separate from the leaves and fall to the ground.

EXAMPLE 5

A solution was prepared by dissolving 18 grams of unmodified corn starch (25-28% amylose and the remainder amylopectin) in water which had been heated to above 200° F. The solids dissolved to produce a film-forming solution having a viscosity of 810 centistokes. This solution sprayed well and was used in the same manner as the solution of Example 1 to treat a geranium plant infested with scale insects. The film was effective in the same manner as that described in Example 1.

In some instances it is desirable to maintain the film in a wet and sticky condition for up to as long as 24 hours. This is for the purpose of trapping insects which were not on the plant at the time the spraying took place. The rate of evaporation can be slowed down by adding a non-toxic salt such as lithium chloride, lithium acetate or potassium acetate in the amount of 10 to 25% by weight.

To insure that the white fly life cycle is broken, it is desirable to repeat the application of the non-toxic insecticide in 14 days. The method of the invention kills the eggs, instars and pupae that make up 20-21 days of the 28 day life cycle. If a toxic insecticide is used which is effective, if at all, in killing flying white flies only, spraying must be repeated in 7 days.

What is claimed is:

1. A method of killing insects, and the eggs of said insects which are protected by a waxy secretion which method comprises applying to a plant infested with said insects an aqueous solution of film-forming corn starch to form a film over said insects to entrap and asphyxiate them in said film.

2. The method of claim 1 in which said insects are selected from the group consisting of whiteflies, scale insects and mealybugs.

3. The method of claim 1 in which said solution is a modified cold water swelling corn starch consisting essentially of amylopectin prepared from intact fully-swollen corn granules as determined by microscopic analysis.

4. The method of claim 3 in which said solution contains borated dextrin in an amount equal to about one-fourth of the amount of said modified cold water swelling corn starch.

5. The method of claim 1 which includes the step of drying said film to cause said film to shrink and separate from said plant.

6. The method of claim 1 in which said solution is applied by spraying initially to form said film over said insects and repeating said spraying step 14 days after said initial spraying.

7. The method of claim 6 which includes the step of drying said film to cause said film to shrink and separate from said plant.

8. A method for killing insects of the order homoptera which exude a protective waxy secretion which method comprises spraying on a plant infested with said insects a corn starch solution containing about 2 to about 5.2% solids to form a film over said insects to entrap and asphyxiate them in said film.

9. The method of claim 8 in which said corn starch is a modified cold water swelling starch consisting essentially of amylopectin prepared from intact fully-swollen corn granules as determined by microscopic analysis.

10. The method of claim 8 in which the spray comprises particles of between 50 and 400 microns.

11. The method of claim 8 in which said solution contains a surface active agent.

12. An insecticide composition, which is not toxic to humans, for killing whiteflies, scale insects and mealybugs on plants comprising an aqueous solution of a modified cold water swelling corn starch consisting essentially of amylopectin prepared from intact fully-swollen corn granules as determined by microscopic analysis and borated dextrin in an amount equal to about one fourth the amount of said modified cold water swelling corn starch, said solution having a kinetic viscosity of from about 3.5 to about 8 centistokes.

* * * * *